US010624923B2

(12) United States Patent
Gutierrez

(10) Patent No.: US 10,624,923 B2
(45) Date of Patent: Apr. 21, 2020

(54) COMPOSITIONS AND RELATED METHODS FOR TREATING AND PREVENTING VIRAL AND RETROVIRAL INFECTIONS

(71) Applicant: Enrique G. Gutierrez, Kissimmee, FL (US)

(72) Inventor: Enrique G. Gutierrez, Kissimmee, FL (US)

( * ) Notice: Subject to any disclaimer, the term of this patent is extended or adjusted under 35 U.S.C. 154(b) by 206 days.

(21) Appl. No.: 15/129,339

(22) PCT Filed: Mar. 25, 2015

(86) PCT No.: PCT/US2015/022513
§ 371 (c)(1),
(2) Date: Sep. 26, 2016

(87) PCT Pub. No.: WO2015/148684
PCT Pub. Date: Oct. 1, 2015

(65) Prior Publication Data
US 2017/0182093 A1 Jun. 29, 2017

Related U.S. Application Data

(60) Provisional application No. 61/967,804, filed on Mar. 26, 2014.

(51) Int. Cl.
| | | |
|---|---|---|
| *A61K 33/24* | (2019.01) | |
| *A61K 45/06* | (2006.01) | |
| *A61K 31/64* | (2006.01) | |
| *A61K 9/14* | (2006.01) | |
| *A61K 9/00* | (2006.01) | |

(52) U.S. Cl.
CPC ............ *A61K 33/24* (2013.01); *A61K 9/0053* (2013.01); *A61K 9/14* (2013.01); *A61K 31/64* (2013.01); *A61K 45/06* (2013.01)

(58) Field of Classification Search
None
See application file for complete search history.

(56) References Cited

U.S. PATENT DOCUMENTS

| | | |
|---|---|---|
| 5,093,327 A | 3/1992 | Gomaille et al. |
| 5,578,606 A | 11/1996 | Vazquez et al. |
| 5,885,980 A | 3/1999 | Gutierrez et al. |
| 2002/0013268 A1 | 1/2002 | Fryburg et al. |
| 2005/0233946 A1 | 10/2005 | Fine et al. |

FOREIGN PATENT DOCUMENTS

| | | |
|---|---|---|
| DE | 43 36 642 A1 | 4/1995 |
| WO | WO 88/00236 A1 | 1/1988 |
| WO | WO 02/24207 A1 | 3/2002 |
| WO | WO 2015/148684 A2 | 10/2015 |

OTHER PUBLICATIONS

Cheng et al. (Journal of Obesity vol. 2011, Article ID 984245 (2011).*
Shigeta et al. (Antiviral Research 58 (2003) 265-271.*
Cusi, et al., "Vanadyl Sulfate Improves Hepatic and Muscle Insulin Sensitivity in Type 2 Diabetes," *Journal of Clinical Endocrinology & Metabolism*, 86(3):1410-1417, (2001).
Proks, et al., "Interaction of Vanadate with the Cloned Beta Cell $K_{ATP}$ Channel," *The Journal of Biological Chemistry*, 274(36):25393-25397, (1999).
Wong, et al., "Physiologically Stable Vanadium (IV) Porphyrins as a New Class of Anti-HIV Agents," *Chem. Commun.*, pp. 3544-3546, (2005).
International Search Report and Written Opinion from PCT/US15/22513, dated Jun. 17, 2015.
D'Cruz, et al., "Potent Dual Anti-HIV and Spermicidal Activities of Novel Oxovanadium(V) Complexes With Thiourea Non-Nucleoside Inhibitors of HIV-1 Reverse Transcriptase," *Biochemical and Biophysical Research Communications*, 302:253-264. (2003).
Rehder, "Vanadium. Its Role for Humans," *Metal Ions in Life Sciences*, 13:139-169, (2013).
Kabadi, et al., "Weight Gain, Improvements in Metabolic Profiles and Immunogenicity with Insulin or Sulphonylurea Administration in AIDS," *Clinical Drug Investigation*, 24(5):287-294, (2004).
Extended European Search Report for EP 15769049, dated Oct. 30, 2017.
Lederman, Michael M., et al. "Residual immune dysregulation syndrome in treated HIV infection." *Advances in immunology*. vol. 119. Academic Press, 2013. 51-83.
Jain, Vivek, et al. "Antiretroviral therapy initiated within 6 months of HIV infection is associated with lower T-cell activation and smaller HIV reservoir size." *The Journal of infectious diseases* 208.8 (2013): 1202-1211.
Ravimohan, Shruthi, et al. "Early immunologic failure is associated with early mortality among advanced HIV—infected adults initiating antiretroviral therapy with active tuberculosis." *The Journal of infectious diseases* 208.11 (2013): 1784-1793.
Lu, Wei, et al. "CD4: CD8 ratio as a frontier marker for clinical outcome, immune dysfunction and viral reservoir size in virologically suppressed HIV-positive patients." *Journal of the International AIDS Society* 18.1 (2015): 20052.

* cited by examiner

*Primary Examiner* — Patricia Duffy
*Assistant Examiner* — Garen Gotfredson
(74) *Attorney, Agent, or Firm* — Morse, Barnes-Brown & Pendleton, P.C.; Stanley F. Chalvire, Esq.

(57) ABSTRACT

Disclosed are pharmaceutical compositions and related methods for treating a subject with a viral or retroviral infection. The disclosed compositions and methods comprise and utilize an effective amount of one or more vanadium-containing compounds and an effective amount of one or more sulfonylureas. In certain embodiments, the viral infection is human immunodeficiency virus (HIV) and the compositions and methods improve one or more immunologic cellular parameters, such as viral load, CD4 counts and CD4/CD8 lymphocyte cell ratios in a subject. Also disclosed are methods of improving one or more immunologic cellular parameters that are associated with viral infections such as HIV in a subject, including viral load, CD4 counts and CD4/CD8 lymphocyte cell ratios.

13 Claims, 8 Drawing Sheets

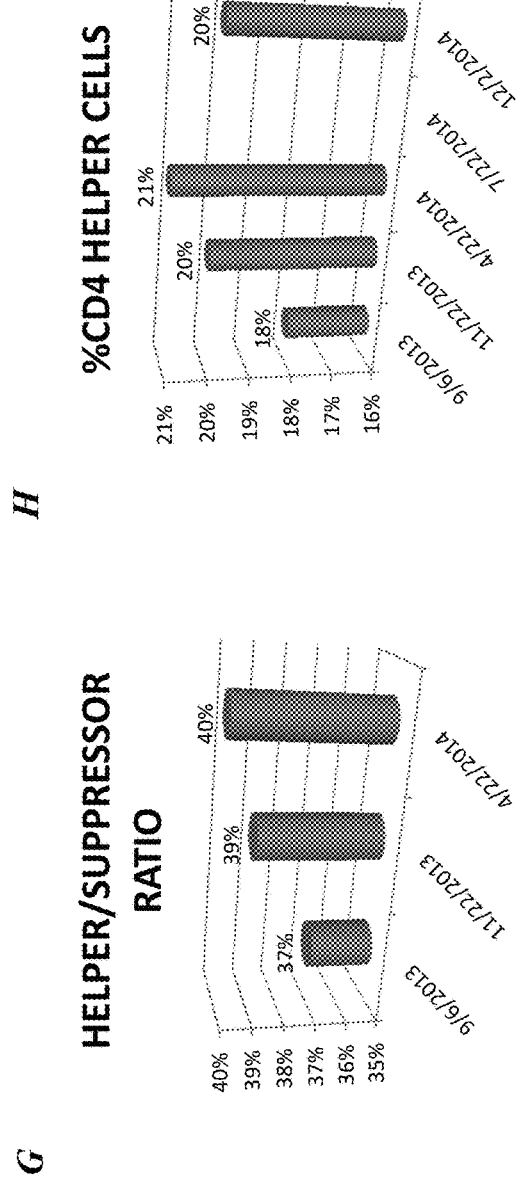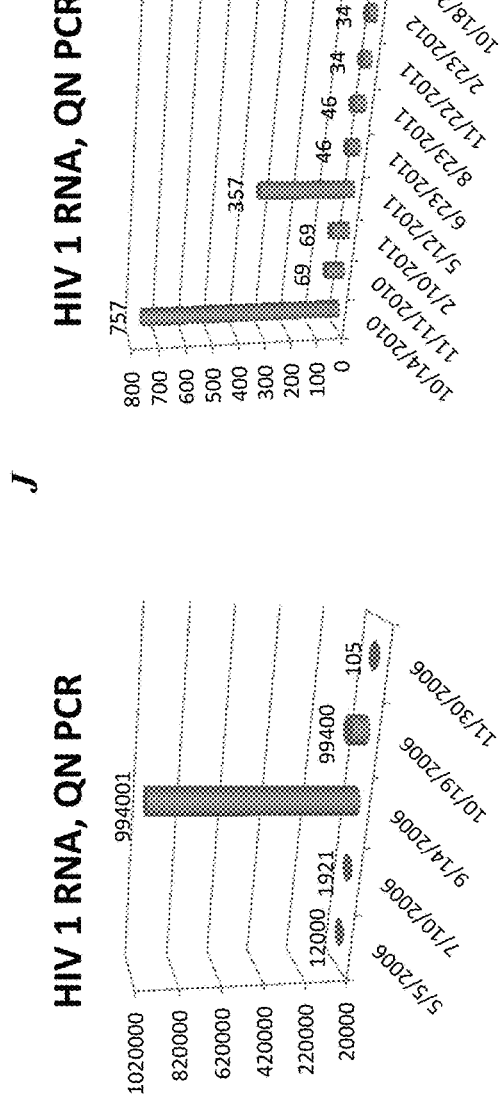
FIGS. 7G-7J

COMPOSITIONS AND RELATED METHODS FOR TREATING AND PREVENTING VIRAL AND RETROVIRAL INFECTIONS

RELATED APPLICATIONS

This application is a national stage filing under 35 U.S.C. 371 of International Application No. PCT/US2015/022513, filed Mar. 25, 2015, which claims the benefit of U.S. Provisional Application Ser. No. 61/967,804, filed Mar. 26, 2014, the entire teachings of which are incorporated herein by reference.

FIELD OF THE INVENTION

The present inventions are generally directed to compositions and related methods of treating and preventing viral and retroviral infections, such as human immunodeficiency virus (HIV). In certain aspects, such compositions and related methods comprise one or more vanadium-containing compounds and one or more sulfonylureas.

BACKGROUND OF THE INVENTION

Vanadyl sulfate ($VOSO_4$), which is readily available over the counter in the United States at local health food stores, is marketed as a nutritional supplement. Although it may be useful for other purposes as well, vanadyl sulfate has historically been taken to improve glycemic control, as described, for example, in U.S. Pat. No. 5,885,980, the entire teachings of which are incorporated herein by reference. Vanadyl sulfate generates the vanadyl radical ($VO^{-3}$) which has been shown to reverse diabetes in pancreatectomized rats. The radical ($VO^{-3}$) is the predominant radical form that is present in extracellular fluid and is reduced intracellularly into the radical ($VO^{+2}$) which is the active form.

Although vanadium-containing compounds such as vanadyl sulfate, have been shown to produce dramatic therapeutic effects in animal models evaluating its effects on glucose metabolism, in human studies these observed effects have been exceedingly weak. It has been thought that inadequate cellular penetration into the human mammalian cell may contribute to the limited effects on glucose metabolism that have been observed in humans (Goldfine, et al., *J. Clin Endocrinol Metab*, 1995, 80 (11): 3311-20; Boden, et al., *Metabolism*, 1996, 45 (9): 1130-1135). Recently, vanadium has also been evaluated as a potential new class of anti-HIV agents (Wong, et al., *Chem. Commun.* (Cambridge), 2005 (28): 3544-3546), however, the virucidal activity of vanadium has not been demonstrated in humans and nor does such evaluation suggest how to address immune deterioration which occurs in human beings following, for example, HIV infection.

New therapeutic strategies are needed for the treatment of viral or retroviral infections such as HIV. Particularly needed are safe and effective compositions and methods for the treatment or eradication of viral and retroviral infections, while improving one or more immunologic cellular parameters associated with such infections.

SUMMARY OF THE INVENTION

The present inventions relate generally to pharmaceutical compositions and to related methods of treating or preventing viral and retroviral infections (e.g., human immunodeficiency virus (HIV)) or otherwise improving immunologic cellular parameters associated with such viral infections (e.g., improving viral load, CD4 counts and CD4/CD8 lymphocyte cell ratios in an HIV-positive subject). The inventions disclosed herein are especially suited for killing pathogens present in target infected cells. For example, in one embodiment the pathogen is a virus such as HIV, and the target infected cells are HIV infected cells.

Also disclosed herein are methods of treating or preventing a viral or retroviral infection in a subject (e.g., a human subject), wherein such methods comprise a step of administering to the subject an effective amount of a vanadium-containing compound (e.g., vanadyl sulfate) and an effective amount of a sulfonylurea (e.g., micronized glyburide), and thereby treating or preventing the viral or retroviral infection. For example, the methods disclosed herein can be practiced to treat or prevent a retroviral infection, such as human immunodeficiency virus (HIV) or acquired immunodeficiency syndrome (AIDS).

Certain immunologic cellular parameters such as, for example, CD4 counts and CD4/CD8 lymphocyte cell ratios, correlate closely with the presence of the pathogenic virus in a subject's body. Accordingly, in certain aspects, the methods disclosed herein are capable of improving one or more immunologic cellular parameters that are associated with a viral or retroviral infection. For example, such methods may be used or practiced to improve one or more immunologic cellular parameters selected from the group consisting of viral load, CD4 counts and CD4/CD8 lymphocyte cell ratios in the subject. Also disclosed are methods of reducing the viral load in a subject and methods of reducing or eliminating the reservoir of replication-competent provirions (e.g., HIV provirions) in a subject. For example, in certain embodiments the methods disclosed herein may be practiced to reduce the viral load in a subject (e.g., an HIV positive subject) to undetectable levels.

In certain aspects the methods disclosed herein comprise the administration of one or more sulfonylureas to the subject, which may be optionally micronized. For example, the sulfonylurea may be selected from the group consisting of glyburide, glipizide, glimepiride, gliclazide, glibenclamide, glibornuride, gliquidone, glisoxepide and glyclopyramide. In certain embodiments, the sulfonylurea is micronized (e.g., micronized glyburide). In certain aspects, an effective amount of the micronized glyburide is from about 0.75 mg to about 12 mg per day.

The methods disclosed herein further comprise the administration of one or more vanadium-containing compounds (e.g., vanadyl sulfate) to the subject (e.g., a mammalian subject). For example, in certain aspects, such vanadium-containing compounds are selected from the group consisting of sodium orthovanadate, sodium metavanadate, bis oxovanadium, sodium metavanadate, vanadyl sulfate, ammonium metavanadate, aluminum orthophosphate vanadia, diperoxovanadate, bis(maltolato)oxovanadium(IV), $VOCl_3$, $VOCl_{21}$, $VCl_3$, peroxovanadium compounds and combinations thereof. In some embodiments, the vanadium-containing compound comprises vanadyl sulfate. In some embodiments, an effective amount of the vanadyl sulfate is from about 10 mg to about 120 mg per day.

In some embodiments, the subject (e.g., a human subject) does not have diabetes. For example, a human subject having or suspected of having an active viral or retroviral infection (e.g., an HIV-positive subject) and that does not have diabetes mellitus may be co-administered one or more vanadium-containing compounds (e.g., vanadyl sulfate) and one or more sulfonylureas (e.g., glyburide).

In certain embodiments, the methods disclosed herein comprise the administration of one or more vanadium-containing compounds and one or more sulfonylureas to the subject for at least one month, at least two months, at least three months, at least four months, at least five months, at least six months, at least nine months, at least twelve months, at least eighteen months, at least twenty-four months, at least thirty-six months, at least forty-eight months or longer.

In certain aspects the methods disclosed herein may further comprise the co-administration of one or more antiviral or antiretroviral compounds to the subject. For example, an HIV-positive subject may be administered one or more vanadium-containing compounds and one or more sulfonylureas as an adjunct therapy that is administered in addition to a primary (e.g., primary antiviral or antiretroviral therapy) to maximize the effectiveness of such primary therapy. In certain embodiments where the subject (e.g., a human subject that does not have diabetes) is HIV-positive, the one or more vanadium-containing compounds and the one or more sulfonylureas may be administered in combination with one or more antiviral or antiretroviral compounds selected from the group consisting of lamivudine, zidovudine, lopinavir, ritonavir, abacavir, tenofovir, emtricitabine, efavirenz, rilpivirine, elvitegravir, cobicistat, dolutegravir, atazanavir, darunavir, raltegravir and any combinations thereof. In certain embodiments, such vanadium-containing compounds (e.g., vanadyl sulfate), sulfonylureas (e.g., micronized glyburide) and antiviral or antiretroviral compounds are administered to the subject in a fixed-dose combination or alternatively are co-packaged together to promote or otherwise improve patient compliance. In certain embodiments, the one or more vanadium-containing compounds and the one or more sulfonylureas may be administered in combination with highly active antiretroviral therapy (HAART).

Also disclosed herein are methods of treating or preventing human immunodeficiency virus (HIV) infection or acquired immunodeficiency syndrome (AIDS) in a subject (e.g., a human subject). Such methods comprise administering to the subject an effective amount of vanadyl sulfate and an effective amount of glyburide (e.g., micronized glyburide). In certain embodiments, such methods are capable of improving one or more immunologic cellular parameters that are associated with the viral or retroviral infection. For example, such methods may be used to improve one or more immunologic cellular parameters selected from the group consisting of viral load, CD4 counts and CD4/CD8 lymphocyte cell ratios in the subject. In certain embodiments, such methods further comprise administering one or more antiviral or antiretroviral compounds to the subject. In certain aspects, the subject does not have diabetes mellitus.

Pharmaceutical compositions for the treatment of a viral or retroviral infection in a subject are also disclosed herein. Also disclosed are pharmaceutical compositions for the treatment of a viral or retroviral infection in a subject. For example, in certain embodiments, such pharmaceutical compositions may be used to reduce or, in certain instances eliminate, the reservoir of replication-competent provirions (e.g., HIV provirions) in a subject. Additionally, disclosed herein are pharmaceutical compositions for reducing viral load in a subject. For example, in certain embodiments the pharmaceutical compositions disclosed herein may be administered to a subject reduce the subject's viral load to undetectable levels. In certain embodiments, such pharmaceutical compositions comprise an effective amount of a vanadium-containing compound (e.g., vanadyl sulfate), an effective amount of a sulfonylurea (e.g., glyburide) and a pharmaceutically acceptable carrier. The vanadium-containing compound may be selected from the group consisting of sodium orthovanadate, sodium metavanadate, bis oxovanadium, sodium metavanadate, vanadyl sulfate, ammonium metavanadate, aluminum orthophosphate vanadia, diperoxovanadate, bis(maltolato)oxovanadium(IV), $VOCl_3$, $VOCl_{2 1}$, $VCl_3$, peroxovanadium compounds and combinations thereof. The sulfonylurea may be selected from the group consisting of glyburide, glipizide, glimepiride, gliclazide, glibenclamide, glibornuride, gliquidone, glisoxepide and glyclopyramide. In certain aspects, such pharmaceutical compositions may further comprise an effective amount of one or more antiviral or antiretroviral compounds. For example, in certain aspects such pharmaceutical compositions may comprise one or more vanadium-containing compounds (e.g., vanadyl sulfate), one or more sulfonylureas (e.g., micronized glyburide) and one or more antiviral or antiretroviral compounds and such compositions may be formulated in a fixed-dose combination.

The above discussed, and many other features and attendant advantages of the present inventions will become better understood by reference to the following detailed description of the invention.

BRIEF DESCRIPTION OF THE DRAWINGS

FIG. 1A illustrates the effect that the administered combination of a vanadium-containing compound and a sulfonylurea had on the subject's absolute CD4 count, expressed in cells/μL. FIG. 1B illustrates the effect that the administered combination of a vanadium-containing compound and a sulfonylurea had on the subject's viral load, as determined by quantifying plasma HIV-1 RNA by way of quantitative PCR and expressed in copies/mL. FIG. 1C illustrates the effects that the administered combination of a vanadium-containing compound and a sulfonylurea had on the subject's helper/suppressor (CD4/CD8) ratio. FIG. 1D illustrates the effects that the administered combination of a vanadium-containing compound and a sulfonylurea had on the subject's CD4 helper cells percentage.

FIG. 2A illustrates the effect that the administered combination of a vanadium-containing compound and a sulfonylurea had on the subject's absolute CD4 count, expressed in cells/μL. FIG. 2B illustrates the effects that the administered combination of a vanadium-containing compound and a sulfonylurea had on the subject's helper/suppressor (CD4/CD8) ratio. FIG. 2C illustrates the effects that the administered combination of a vanadium-containing compound and a sulfonylurea had on the subject's CD4 helper cells percentage. FIG. 2D illustrates the effect that the administered combination of a vanadium-containing compound and a sulfonylurea had on the subject's viral load, as determined by quantifying plasma HIV-1 RNA by way of quantitative PCR and expressed in copies/mL.

FIG. 3A illustrates the effect that the administered combination of a vanadium-containing compound and a sulfonylurea had on the subject's absolute CD4 count, expressed in cells/µL. FIG. 3B illustrates the effects that the administered combination of a vanadium-containing compound and a sulfonylurea had on the subject's helper/suppressor (CD4/CD8) ratio. FIG. 3C illustrates the effects that the administered combination of a vanadium-containing compound and a sulfonylurea had on the subject's CD4 helper cells percentage. FIG. 3D illustrates the effect that the administered combination of a vanadium-containing compound and a sulfonylurea had on the subject's viral load, as determined by quantifying plasma HIV-1 RNA by way of quantitative PCR and expressed in copies/mL.

FIG. 4A illustrates the effect that the administered combination of a vanadium-containing compound and a sulfonylurea had on the subject's absolute CD4 count, expressed in cells/µL. FIG. 4B illustrates the effects that the administered combination of a vanadium-containing compound and a sulfonylurea had on the subject's helper/suppressor (CD4/CD8) ratio. FIG. 4C illustrates the effects that the administered combination of a vanadium-containing compound and a sulfonylurea had on the subject's CD4 helper cells percentage. FIG. 4D illustrates the effect that the administered combination of a vanadium-containing compound and a sulfonylurea had on the subject's viral load, as determined by quantifying plasma H1V-1 RNA by way of quantitative PCR and expressed in copies/mL.

FIG. 5A illustrates the effect that the administered combination of a vanadium-containing compound and a sulfonylurea had on the subject's absolute CD4 count, expressed in cellsµL. FIG. 5B illustrates the effects that the administered combination of a vanadium-containing compound and a sulfonylurea had on the subject's helper/suppressor (CD4/CD8) ratio. FIG. 5C illustrates the effects that the administered combination of a vanadium-containing compound and a sulfonylurea had on the subject's viral load, as determined by quantifying plasma HIV-1 RNA by way of quantitative PCR and expressed in copies/mL. FIG. 5D illustrates the effects that the administered combination of a vanadium-containing compound and a sulfonylurea had on the subject's CD4 helper cells percentage.

FIG. 6A illustrates the effect that the administered combination of a vanadium-containing compound and a sulfonylurea had on the subject's absolute CD4 count, expressed in cellsµL. FIG. 6B illustrates the effects that the administered combination of a vanadium-containing compound and a sulfonylurea had on the subject's helper/suppressor (CD4/CD8) ratio. FIG. 6C illustrates the effects that the administered combination of a vanadium-containing compound and a sulfonylurea had on the subject's CD4 helper cells percentage. FIG. 6D illustrates the effect that the administered combination of a vanadium-containing compound and a sulfonylurea had on the subject's viral load, as determined by quantifying plasma HIV-1 RNA by way of quantitative PCR and expressed in copies/mL.

FIGS. 7A-F illustrates the effect that the administered antiretroviral medications had on the subject's absolute CD4 count, expressed in cells/µL.

FIGS. 7G-J illustrate improvements in immune cellular parameters that were observed in an HIV-positive subject that was administered standard antiretroviral medications without the combination of a vanadium-containing compound and a sulfonylurea. FIG. 7G illustrates the effects that the administered antiretroviral medications had on the subject's helper/suppressor (CD4/CD8) ratio. FIG. 7H illustrates the effects that the administered antiretroviral medications had on the subject's CD4 helper cells percentage. FIGS. 7I-J illustrate the effect that the administered antiretroviral medications had on the subject's viral load, as determined by quantifying plasma HIV-1 RNA by way of quantitative PCR and expressed in copies/mL.

DETAILED DESCRIPTION OF THE INVENTION

Figures 1A, 1B, 1C, 1D:
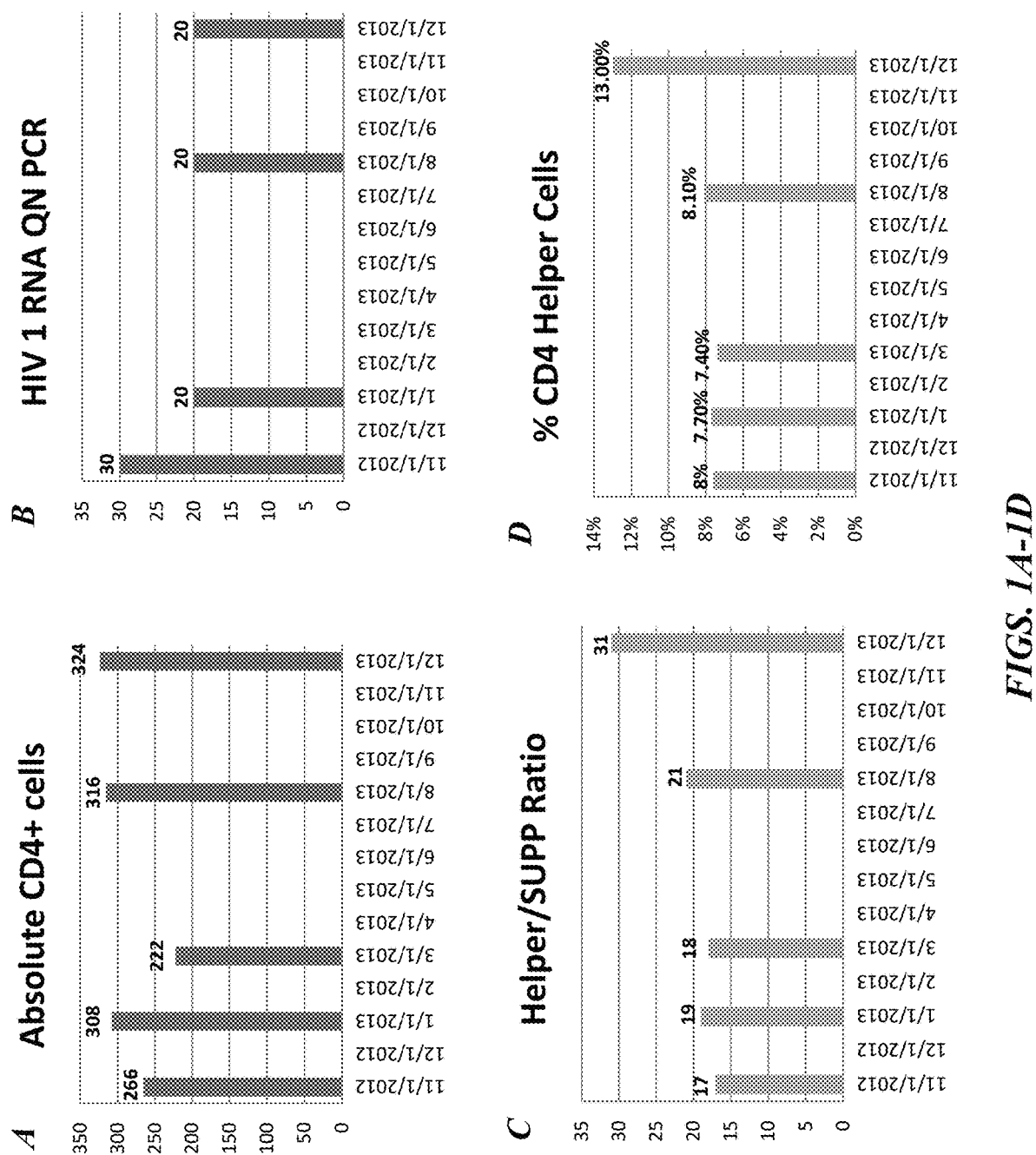
FIGS. 1A-D demonstrate the improvements in immune cellular parameters that were observed in an HIV-positive subject that was administered a combination of a vanadium-containing compound and a sulfonylurea.

The present inventions are generally directed to compositions (e.g., pharmaceutical compositions) and to related methods of treating viral or retroviral infections, such as human immunodeficiency virus (HIV) and acquired immune deficiency syndrome (AIDS), and to improving certain immunologic cellular parameters that may be associated with such viral infections (e.g., CD4 counts and CD4/CD8 lymphocyte cell ratios in an HIV-positive subject). The inventions disclosed herein are particularly suited for killing pathogens (e.g., viral pathogens) that may be present in an infected cell. For example, in certain embodiments the present invention may be used to kill a viral pathogen such as HIV, by targeting cells that are infected with the HIV virus.

In certain embodiments, the compositions and methods disclosed herein generally comprise a combination of an effective amount of one or more vanadium-containing compounds (e.g., vanadyl sulfate) and an effective amount of one or more sulfonylureas (e.g., micronized glyburide). As used herein, the term "vanadium-containing compound" is intended to encompass any compounds which form or produce the vanadium oxide $VO^{+2}$ radical in, for example, a subject's body or cells. In certain embodiments, the vanadium-containing compound (e.g., vanadyl sulfate) forms such $VO^{+2}$ radical intracellularly upon or following its administration (e.g., oral or parenteral administration) to a subject. It is believed that the $VO^{-3}$ radical is reduced after entry into the cells to yield the radical $VO^{+2}$. Since vanadium readily changes oxidation state, it is preferred to describe the therapeutic amounts of vanadium-containing compounds on the basis of the weight of the element vanadium.

Vanadium inhibits the $(Na^{++}K^+)$-ATPase enzyme and the $Na^+$, $K^+$ pump and has been shown to bind to the phosphate residue of the $(Na^{++}K^+)$-ATPase enzyme. It has been shown that vanadate exerts its activity through the sulfonylurea receptor subunit (Proka, et al. *J. Biol. Chem.*, 1999, 274 (36): 25393-25397). Exemplary vanadium-containing compounds include, without limitation, sodium orthovanadate, sodium metavanadate, bis oxovanadium, sodium metavanadate ($NaVO_3$), vanadyl sulfate ($VOSO_4$), sodium orthovanadate ($Na_3\ VO_4$), ammonium metavanadate($NH_4VO_3^-$), aluminum orthophosphate vanadia ($V_2O_5^-AIPO_4$), diperoxovanadate, bis(maltolato)oxovanadium(IV) (BMOV), $VOCl_3$, $VOCl_{21}$ VCb, peroxovanadium (pv)compounds, $K_2[VO(O_2)_2$ (picolinato)] 2 $H_2O$)[bpv(pic)] $VO(O_2)$(picolinato)($H_2O$)2[MPV(pic)], and the like. In certain embodiments, the preferred vanadium-containing compound is vanadyl sulfate due to its lower levels of toxicity relative to other vanadium-containing compounds.

The compositions and methods disclosed herein also generally comprise an effective amount of one or more sulfonylureas such as, for example, glyburide. In certain embodiments, the sulfonylurea is micronized (e.g., micronized glyburide) or is characterized by small particle sizes in the micron range. Exemplary sulfonylureas include, without limitation, glyburide, glipizide, glimepiride, gliclazide, glibenclamide, glibornuride, gliquidone, glisoxepide and glyclopyramide, any of which may be optionally micronized. Sulfonylureas such as glyburide bind firmly to the 140 kda protein of the potassium channel, also referred to as the sulfonylurea receptor. Glyburide is the most biochemically-potent stimulator of the sulfonylurea receptor because of the characteristic of its constant action associated to its firm binding to the sulfonylurea receptor deep at the 140 kda protein site.

As used herein, the term "effective amount" means an amount sufficient to achieve a meaningful benefit to the subject (e.g., treating, modulating, curing, preventing and/or ameliorating the underlying viral disease). For example, an effective amount of the vanadium-containing compounds that are the subject of the present inventions may be generally determined based on the activity of such compounds and the amount of such compounds that are absorbed by the subject following its oral administration. Generally, the amount of compound administered to a subject in need thereof will depend upon the characteristics of the subject and the severity of their disease. Such characteristics include the condition, general health, age, subjective symptoms, objective appearance, sex and body weight of the subject.

An effective amount of a vanadium-containing compound (e.g., vanadyl sulfate) necessary to treat viral or retroviral infections in accordance with the present inventions is generally in the range of from about 30 mg/day to 120 mg/day, or preferably from about 60 mg/day to 120 mg/day for a human subject of standard body weight (e.g., 150-160 pounds). One of ordinary skill in the art will be readily able to determine an effective amount depending on these and other related factors. For example, vanadyl sulfate ($VOSO_4$) can generally be administered in an amount of from about 10 mg/day to 120 mg/day, preferably from about 30 mg/day to 90 mg/day, and most preferably from about 60 mg/day to 90 mg/day. The required dosage amount may be administered once, twice, three times, four times or up to several times a day. In certain embodiments, an effective amount of a vanadium-containing compound is administered to the subject at least once a day (e.g., 60 mg of vanadyl sulfate once daily).

An effective amount of a sulfonylurea (e.g., micronized glyburide) necessary to treat viral or retroviral infections in accordance with the present inventions is generally in the range of from about 0.75 mg/day to 12 mg/day, preferably from about 1.25 mg/day to 9 mg/day, most preferably from about 3 mg/day to 7.5 mg/day for a human subject of standard body weight (e.g., 150-160 pounds). Micronized glyburide may be administered in accordance with the present invention as a single dose or up to four times daily, preferably in one dose with the vanadium-containing compound as previously described.

The one or more vanadium-containing compounds (e.g., vanadyl sulfate) and one or more sulfonylurea (e.g., micronized glyburide) may be co-administered in separate dosage forms, or formulated in a fixed-dose combination dosage form. In those embodiments where the vanadium-containing compound and sulfonylurea are co-administered separately, preferably such agents are administered at or about the same time. In those embodiments where an effective amount of the vanadium-containing compound and sulfonylurea are formulated into a single pharmaceutical composition, such composition may be formulated for oral administration (e.g., in the form of tablets, capsules, caplets, soft gel capsules and the like).

The combination of the vanadium-containing compound and sulfonylurea (e.g., micronized glyburide) may be administered to the subject over a period of up to 9 months or longer, preferably from about 3 weeks to 9 months, and most preferably from about 6 months to 9 months. Shorter or longer periods of treatment can be employed depending on the subject's response (e.g., by observing improvements in one or more of the subject's immunologic cellular parameters, such as the subject's absolute CD4 cell count). Once the desired response is achieved the combination of the vanadium-containing compound and the sulfonylurea can be administered indefinitely without any significant adverse or side effects.

In addition to treating viral or retroviral infections (e.g., HIV), the compositions and methods disclosed herein may be used to improve one or more immunologic cellular parameters that are associated with such a viral infection (e.g., absolute CD4 cell counts and CD4/CD8 lymphocyte cell ratios) or that otherwise correlate with the presence of a pathogenic virus in the subject's body. As used herein, the phrase "immunologic cellular parameters" generally refers to any immunological and/or hematological objective parameters that may be used to assess or monitor a subject's condition (e.g., a viral or retroviral infection), the progression of disease and/or the efficacy of the inventions disclosed herein. In certain embodiments (e.g., where the retroviral infection is HIV), the immunologic cellular parameters are selected from the group consisting of CD4 counts and CD4/CD8 lymphocyte cell ratios. In certain embodiments, the phrase "immunologic cellular parameters" includes a subject's viral load and accordingly, in such embodiments, the immunologic cellular parameters are selected from the group consisting of viral load, CD4 counts and CD4/CD8 lymphocyte cell ratios. As used herein, the term "viral load" refers to the concentration or number of copies of a virus (e.g., HIV) detected in the blood or serum of a subject. In certain embodiments where the subject is HIV-positive, the compositions and methods disclosed herein reduce or eliminate a subject's viral load. In certain embodiments, the compositions and methods disclosed herein reduce or eliminate the reservoir of replication-competent provirions that may persist during treatment with highly active antiretroviral therapy (HAART) within the CD4 T-cells and which contribute to the disease burden. For example, in certain embodiments the compositions and methods disclosed herein may be used to reduce an HIV-positive subject's viral load to undetectable levels. Similarly, in certain embodiments the compositions and methods disclosed herein may be used to reduce or eliminate the reservoir of replication-competent provirions (e.g., HIV provirions) to undetectable levels.

In a preferred embodiment of the present invention, the method of improving immunologic cellular parameters includes administering to the subject of from about 60 mg to 90 mg of vanadyl sulfate and 3 mg to 12 mg of micronized glyburide once daily, preferably in the morning for at least 8 weeks and up to 9 months until a response is noted with normalization of immunologic cellular parameters including CD4 counts and CD4/CD8 lymphocyte cell ratios at the normal or near normal ranges.

The active agents of the present invention (e.g. vanadyl sulfate and micronized glyburide) are commercially available and can be utilized as such in the present invention. However, if fixed combination dosages forms are desired, they may be formulated by grinding each of the commercially available components together and placing the appropriate amount of the combination in an appropriate dosage delivery form (e.g. capsule or tablet) by known techniques. Alternatively, the active components may be optionally mixed along with pharmaceutically acceptable carriers (e.g. cornstarch, lactose, lecithin, soybean oil, glycerine and the like) as desired, and the mixture put up into an appropriate dosage form. The methods of preparing the pharmaceutical compositions of the present invention and selection of pharmaceutically acceptable carriers and excipients are described in detail in, for example, L. William, Remington: The Science and Practice of Pharmacy. $22^{nd}$ ed. Pharmaceutical Press (2012), the entire contents of which are incorporated herein by reference. In a preferred embodiment of the present invention, the pharmaceutical composition is formulated into a dosage form (e.g., a tablet or capsule) comprising 3 mg glyburide and 60 mg vanadyl sulfate.

It should be noted that the pharmaceutical compositions disclosed herein may be administered to a subject via any suitable route of administration, including one or more of the topical, transdermal, buccal, sublingual, oral or parenteral routes of administration. In certain embodiments, such pharmaceutical compositions may be administered to a subject orally. In certain other embodiments, such pharmaceutical compositions are administered to a subject intravenously.

The compositions and methods disclosed herein may be administered alone or as an adjunct therapy in combination with antiviral or antiretroviral compounds. For example, in those embodiments where the compositions and methods of the present invention are used to treat an HIV-positive subject, such compositions and methods may be administered in combination with antiretroviral therapy (e.g., in a combination with a combination of at drugs that suppress HIV replication). In certain embodiments, the composition and methods disclosed herein are administered in combination with HAART. For example, one or more vanadium-containing compounds and one or more sulfonylureas may be administered, formulated or packaged in combination with one, two, three or more antiviral or antiretroviral compounds selected from the group consisting of lamivudine, zidovudine, lopinavir, ritonavir, abacavir, tenofovir, emtricitabine, efavirenz, rilpivirine, elvitegravir, cobicistat, dolutegravir, atazanavir, darunavir, raltegravir and any combinations thereof.

While in certain embodiments, the inventions disclosed herein contemplate the treatment of viral or retroviral infections such as HIV and AIDS, it should be understood that the utility of such inventions are not limited to HIV. Rather, the compositions and methods disclosed herein are useful for treating any viral or retroviral infections. For example, in certain embodiments, the compositions and methods disclosed herein may be used for the treatment of one or more of Dengue fever, Japanese encephalitis, West Nile encephalitis, Yellow fever, Hepatitis C, Epstein-Barr virus, Ebola virus, Herpes simplex virus 1 and 2, respiratory syncytial virus, influenza, human papillomavirus and others. In such embodiments, the inventions disclosed herein may also be administered in combination with standard antiviral or antiretroviral compounds or medications.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compounds, compositions and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of; such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

AB is 59 year old man who was diagnosed as being HIV-positive on Jul. 18, 2011. At the time of diagnosis AB had advanced immunosuppression and *Pneumocystis carinii* pneumonia (PCP). AB's CD4% count was 2.3%, his absolute CD4 count was 18 cells/µL, his CD4/CD8 ratio was 0.1, and his viral load was 325,444 copies/mL.

AB was originally placed on a fixed-dose combination of emtricitabine, tenofovir and efavirenz (ATRIPLA) in September 2011. In December 2012, AB's therapy was changed to tenofovir and emtricitabine (TRUVADA) and efavirenz (SUSTIVA), yet his immune system remained in a decompensated state. In March 2013, AB was prescribed and began taking 6 mg of micronized glyburide twice daily and 30 mg of vanadyl sulfate daily for 4 months without improvement in immunologic cellular parameters, at which point the administered dose of vanadyl sulfate was increased to 60 mg daily, resulting in the observed improvement of immunologic cellular parameters, as shown in FIG. 1.

As illustrated in FIG. 1, within months of initiating therapy with micronized glyburide and vanadyl sulfate, dramatic improvements in immune cellular parameters were observed. The observed improvements in AB's CD4 counts and CD4/CD8 ratio suggest that the administered combination of micronized glyburide and vanadyl sulfate produced a profound positive effect on AB's immune health and further suggest depletion of HIV virus reservoirs due to intracellular killing of the virus.

Example 2

DC is a 63 year old woman who was diagnosed as being HIV-positive in 1989 and subsequently developed AIDS in 2000. DC had personally observed several of her own friends suffer from complications relating to antiviral therapies and, as a result, she has not been compliant to prescribed antiviral therapy, except for a maximum period of two to three months. In particular, DC has been uncompliant with her prescribed antiviral therapy, typically going without treatment for months until she develops lymphadenopathy and thrush, following which she then reinitiated her antiviral therapy.

Figures 2A, 2B, 2C, 2D:
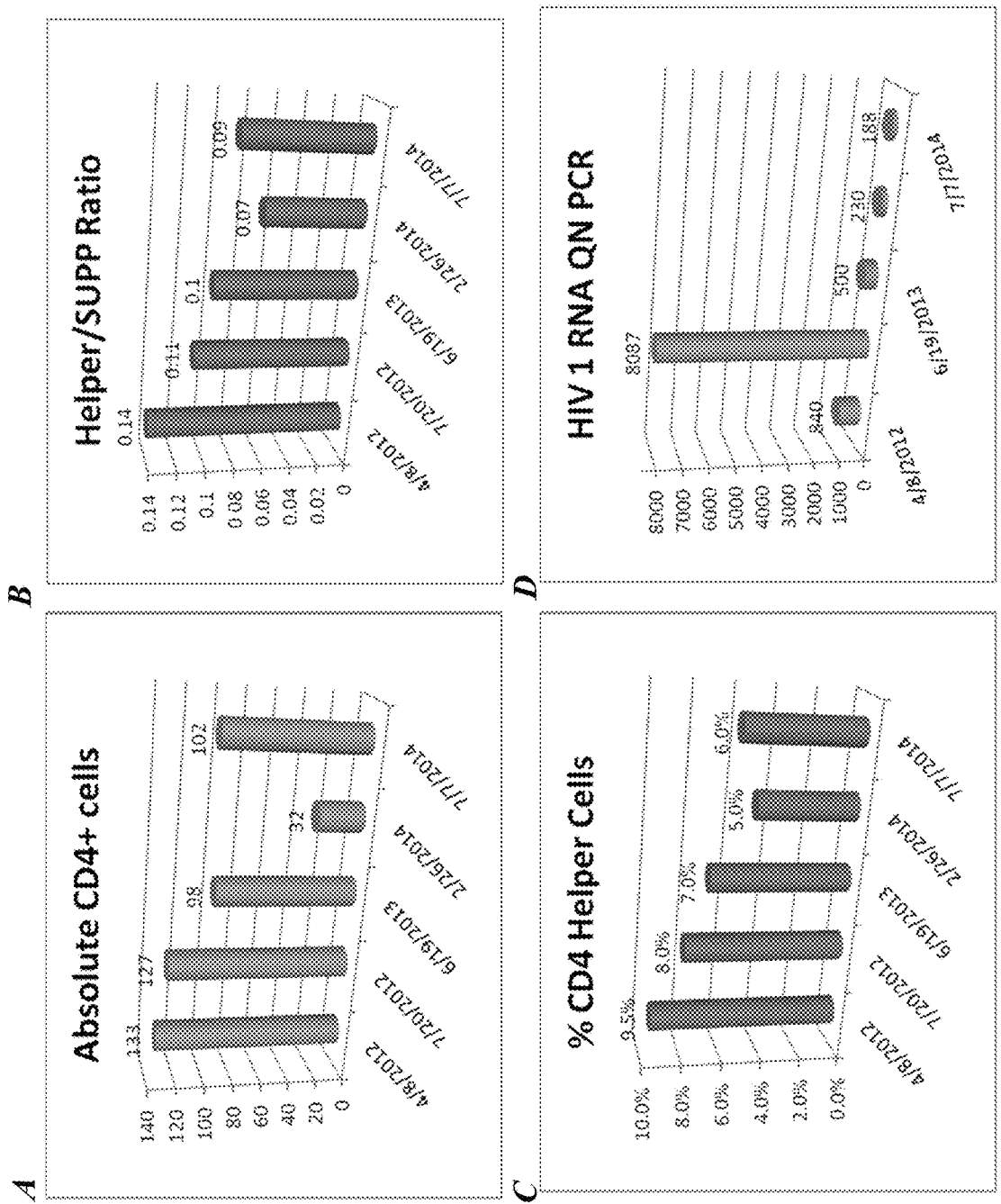
FIGS. 2A-D illustrate the improvements in immune cellular parameters that were observed in an HIV-positive subject that was administered a combination of a vanadium-containing compound and a sulfonylurea.

When DC does take antiviral medications, she will only use raltegravir (ISENTRESS), etravirine (INTELENCE) and lamivudine (EPIVIR). It was recommended that DC initiate adjunct therapy with micronized glyburide and vanadyl sulfate; however, until about July 2013, DC had refused to comply with the recommended adjunct therapy and instead elected to use only one of the two components of the recommended therapy, which, as shown in FIG. 2D resulted in dramatic reductions in her viral load, reducing the number of copies of the HIV from 8,087 viral copies to 500 viral copies within several weeks. Paradoxically, DC was still in severe immunologic failure, suggesting extracellular effects of the therapy.

In March 2014, DC elected to fully comply with the recommended therapy of micronized glyburide and vanadyl sulfate and, as shown in FIG. 2A, within a few months DC's absolute CD4 counts increased from 32 to 102. During the period of February 2014 to July 2014, significant improvements in CD4 counts were observed, as illustrated in FIG. 2A, however the number of HIV viral copies have remained persistently low regardless of the cell counts, as illustrated in FIG. 2D. This observation suggests that therapy with micronized glyburide and vanadyl sulfate has a profound virucidal effect at the level of the genomic provirions.

Example 3

HH is a 31 year old woman and has been HIV-positive for over ten years. HH had a history of non-compliance with prescribed antiviral therapy and had developed anti-retroviral resistance. After having been without treatment for several months, HH presented for care in November 2012, prior to which she stated had been treated with a fixed-dose combination of emtricitabine, tenofovir and efavirenz (ATRIPLA).

HH was not responding to her antiviral therapy and was empirically started on a fixed-dose combination of tenofovir and emtricitabine (TRUVADA) and efavirenz (SUSTIVA) in July 2013. immunologic competence continued deteriorating and in April 2014, HH was placed on opportunistic infection prophylaxis for immunologic failure. HH was then placed on abacavir sulfate (EPZICOM), ritonavir (NORVIR) and darunavir (PREZISTA) in May 2014. At this time adjunct therapy with 3 mg micronized glyburide and 60 mg vanadyl sulfate was also initiated.

Figures 3A, 3B, 3C, 3D:
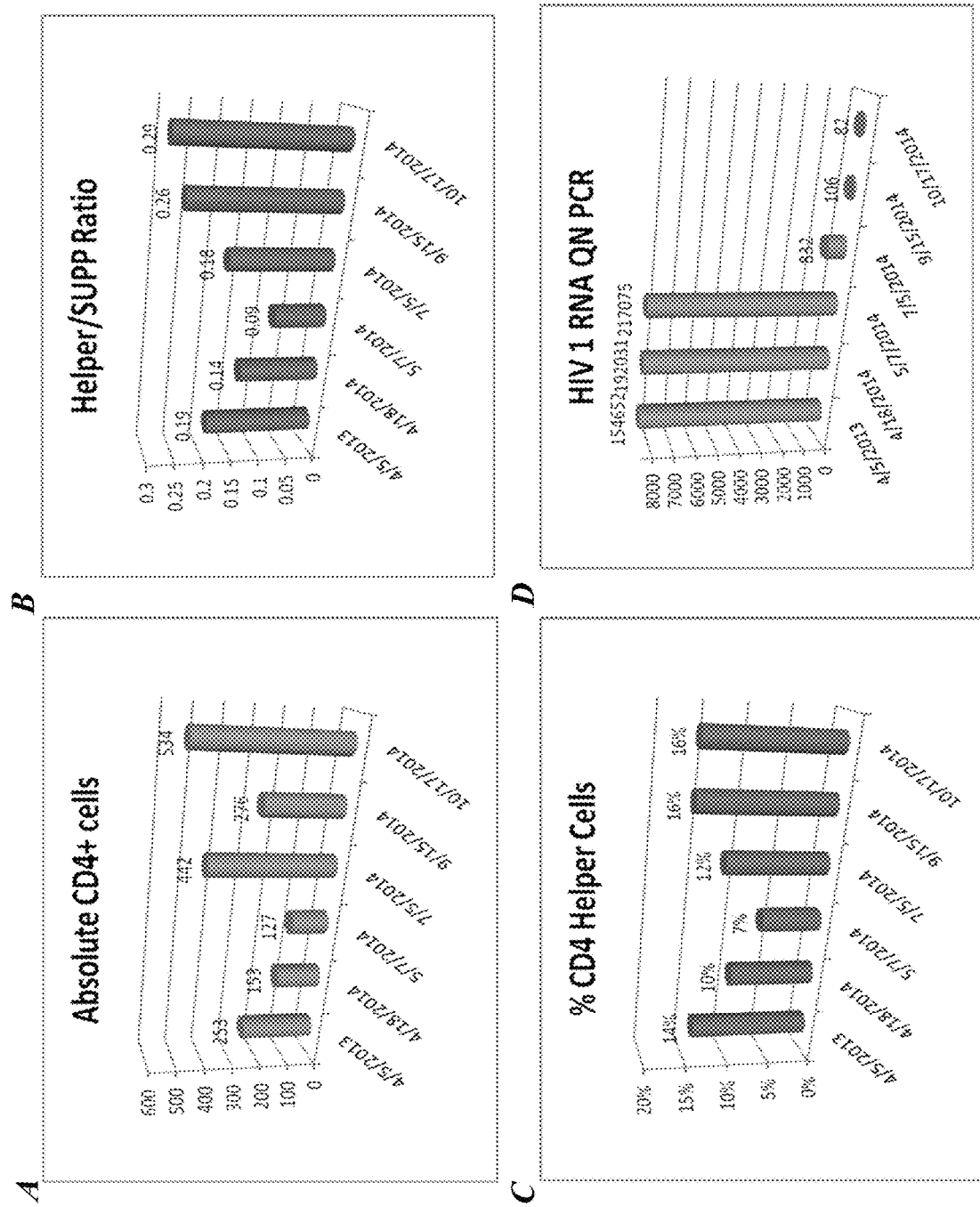
FIGS. 3A-D illustrate the improvements in immune cellular parameters that were observed in an HIV-positive subject that was administered a combination of a vanadium-containing compound and a sulfonylurea.

As illustrated in FIGS. 3A and 3D, within approximately one month, HH's absolute CD4 lymphocyte count increased from 127 cells/µL to 442 cells/µL, while her viral load dropped from 217,075 copies to 832 copies. Under conventional antiretroviral therapy the observed improvements in cell counts are perhaps 10 to 100 fold slower that those observed in the present study. The foregoing therefore suggests that since therapy with micronized glyburide and vanadyl sulfate involves a nonspecific virucidal agent with genomic actions with a cellular transport system, the vanadium-containing vanadyl sulfate may be destroying the provirions in the intracellular reservoirs and the free virus in the blood stream.

Example 4

WM a 47 year old man who presented for care in June 2014, upon released from a one month hospitalization due to respiratory failure resulting from to *Pneumocystis carinii* pneumonia (PCP), where he was newly diagnosed with symptomatic AIDS. Therapy with 6 mg micronized glyburide and 60 mg vanadyl sulfate was also proposed and initiated at this time to reconstitute his immune system and avoid opportunistic infections.

Figures 4A, 4B, 4C, 4D:
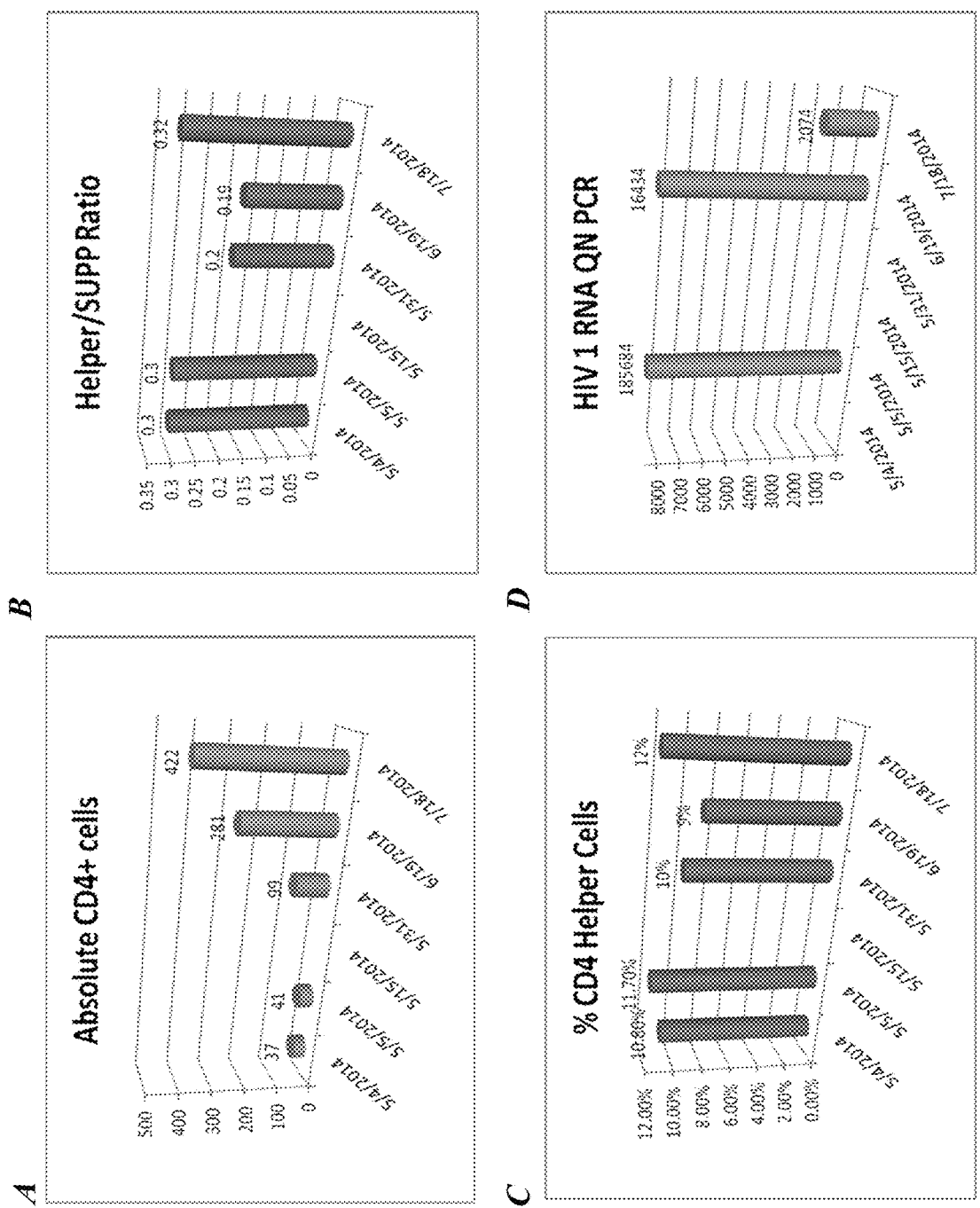
FIGS. 4A-D illustrate the improvements in immune cellular parameters that were observed in an HIV-positive subject that was administered a combination of a vanadium-containing compound and a sulfonylurea.

As illustrated in FIG. 4A, a marked improvement in WM's absolute CD4 lymphocyte counts from 288 cells/µL to 422 cells/µL was observed within one month of having initiating therapy with micronized glyburide and vanadyl sulfate. Similarly, as illustrated in FIG. 4D, a reduction in WM's viral load from 16,434 copies to 2,074 copies was observed within one month of initiating therapy. The rapid and almost complete restoration of the immune system that was observed following the initiation of therapy with micronized glyburide and vanadyl sulfate could not have resulted from only inhibition of HIV viral replication by the antiretroviral medications, but rather suggests direct virucidal actions by such therapy at the genomic level.

Example 5

TW is a 44 year old man who presented for care in March 2013 with a twenty year history of HIV and who had been undergoing antiretroviral treatment since 2010. TW had achieved appropriate viral suppression yet his immune system remained impaired and had remained this way for many years.

Figures 5A, 5B, 5C, 5D:
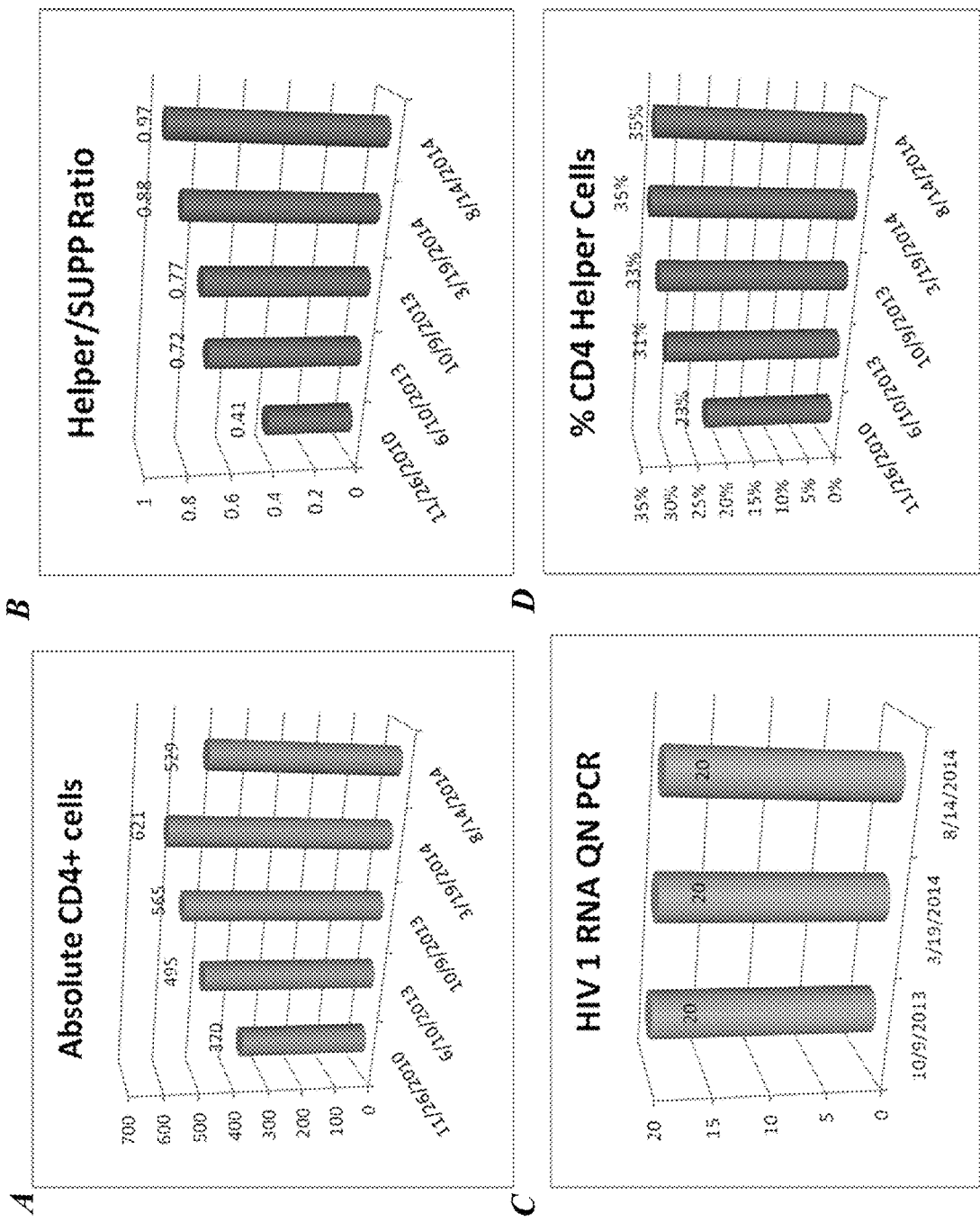
FIGS. 5A-D illustrate the improvements in immune cellular parameters that were observed in an HIV-positive subject that was administered a combination of a vanadium-containing compound and a sulfonylurea.
Figure 6A:
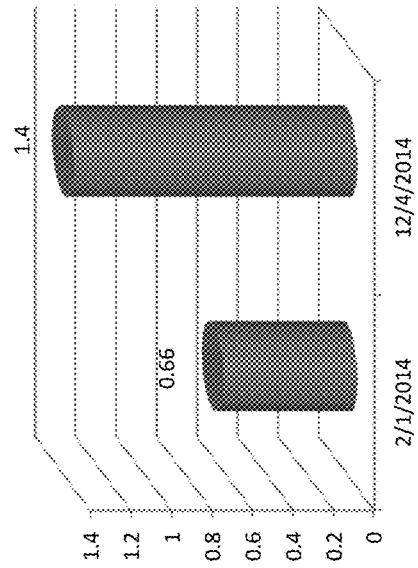
FIGS. 6A-D illustrate the improvements in immune cellular parameters that were observed in an HIV-positive subject that was administered a combination of a vanadium-containing compound and a sulfonylurea.
Figure 6B:
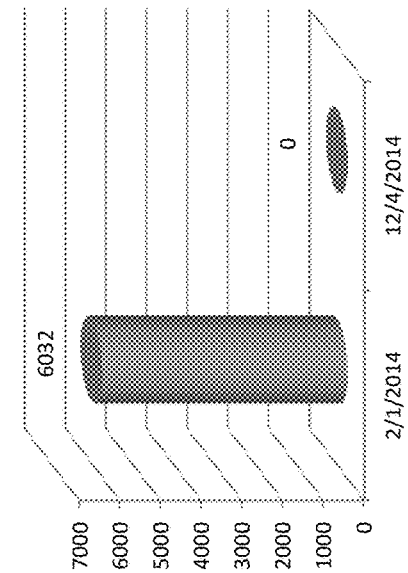
Figure 6C:
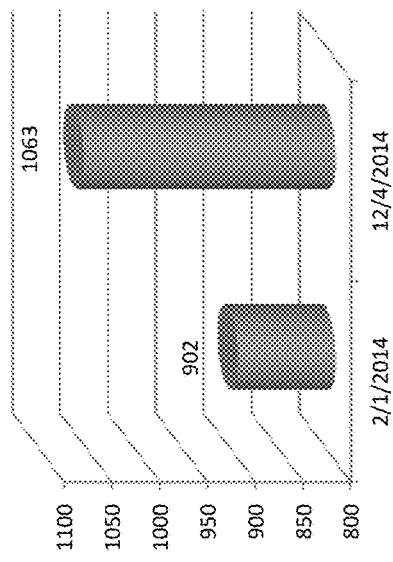
Figure 6D:
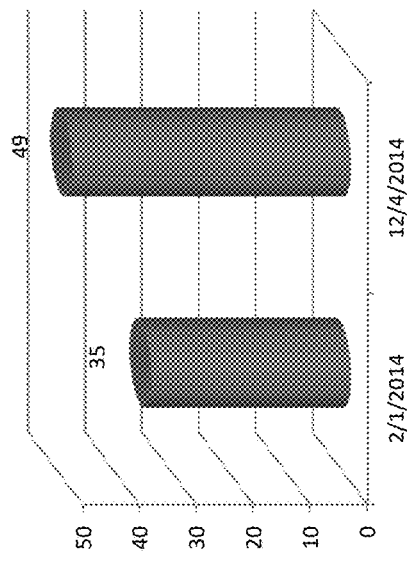

Adjunct therapy with 3 mg micronized glyburide and 60 mg vanadyl sulfate was also proposed and initiated. As illustrated in FIG. 5, since having initiated such adjunct therapy TW has experienced a steady and consistent improvement in his immune cellular parameters. In particular, the observed normalization of his CD4 lymphocyte counts (FIG. 5A) and significant improvements in his CD4/CD8 ratio (FIG. 5B) suggest depletion of viral reservoirs.

Example 6

PL is a 43 year old woman newly diagnosed as being HIV-positive and who presented for care in October 2014. PL has had a positive response to standard antiretroviral therapy with emtricitabine, rilpivirine, and tenofovir (COMPLERA), yet her immune cellular parameters were not optimal.

Adjunct therapy with 3 mg of micronized glyburide and 60 mg of vanadyl sulfate was also proposed and initiated in October 2014 and, within 2 months significant improvement in immune cellular parameters were observed, as illustrated in FIG. 6. PL has continued the adjunct therapy without any adverse effects or hypoglycemia even though she is not a diabetic.

Example 7

JB is an HIV-positive male subject who presented for care after having previously received standard medical treatment with antiretroviral medications from another clinic. JB had not been prescribed a course of micronized glyburide and vanadyl sulfate.

Figures 7A, 7B, 7C, 7D, 7E, 7F:
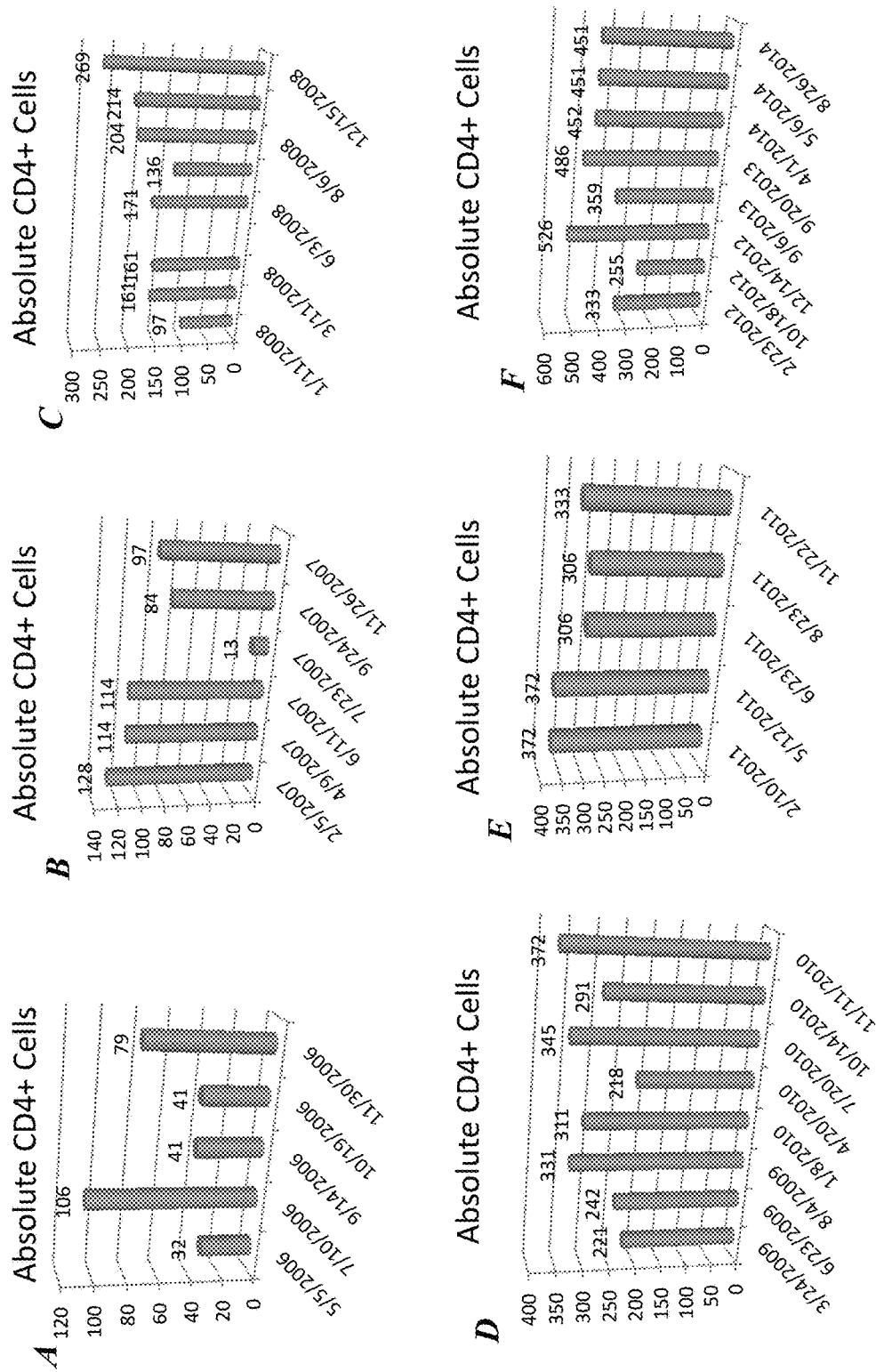
FIGS. 7A-F illustrate improvements in immune cellular parameters that were observed in an HIV-positive subject that was administered standard antiretroviral medications without the combination of a vanadium-containing compound and a sulfonylurea. In particular.

As illustrated in FIGS. 7I-J, the standard treatment appeared to have been effective at suppressing HIV viral counts, as illustrated by the observed reductions in his number of HIV viral copies. As illustrated in FIGS. 7A-H, however, the cellular response to standard therapy appeared to be sluggish and his observed improvements in immunologic cellular parameters such as his absolute CD4+ cell counts, did not achieve or approximate normal lymphocyte concentrations.

Discussion

The present inventor has determined that it is possible to insert a potent antiviral into the intracellular compartment which is capable of killing the virus and the provirions and block further viral cell penetration. This, when achieved, resulted in increased CD4 cell count and normalization of the CD4/CD8 cell ratios.

Without wishing to be bound by any particular theory, it is believed that the potassium channel provides a method of achieving a doorway penetration into the intracellular compartment in the human mammalian cell by using vanadium, a sulfonylurea 2 (SUR2) agonist, and micronized glyburide, a potent sulfonylurea 1 (SUR 1) agonist. It is believe that the intracellular introduction of the virucidal vanadium complex kills the virus and further blocks entry via the CCR5 receptor, thereby achieving cures. Direct viral killing by vanadium and disruption of provirions genomic attachment and replication indicates that this method could be a potential cure to viral or retroviral infectious diseases, such as HIV. Manipulation of the sulfonylurea receptors in the potassium channels plays a critical role in vanadium penetration and biological action in human mammalian cells.

The improvement in immune function demonstrated in the foregoing Examples are surprising and unexpected, at least because the CD4 T lymphocyte counts increase significantly and the CD4/CD8 lymphocyte ratios improved dramatically. These surprising and unexpected observations suggest reductions in immune activation in view of reduced CD5 counts and increase in CD4 counts and further suggest reductions in viral reservoir and disease burden leading to immune reconstitution and restoration.

What is claimed is:

1. A method of improving one or more of CD4 counts and CD4/CD8 lymphocyte cell ratios in a subject having a retroviral infection selected from the group consisting of human immunodeficiency virus (HIV) and acquired immunodeficiency syndrome (AIDS), the method comprising administering to the subject an effective amount of vanadyl sulfate and an effective amount of glyburide, thereby improving one or more of the CD4 counts and CD4/CD8 lymphocyte cell ratios in the subject.

2. The method of claim 1, wherein the retroviral infection is human immunodeficiency virus (HIV).

3. The method of claim 1, wherein the glyburide is micronized.

4. The method of claim 3, wherein an effective amount of the micronized glyburide is from about 0.75 mg to about 12 mg per day.

5. The method of claim 1, wherein an effective amount of the vanadyl sulfate is about 60 mg to about 120 mg per day.

6. The method of claim 1, wherein the subject does not have diabetes mellitus.

7. The method of claim 1, further comprising administering one or more antiviral or antiretroviral compounds to the subject.

8. A method of improving one or more of CD4 counts and CD4/CD8 lymphocyte cell ratios in a subject in need thereof and having human immunodeficiency virus (HIV) or acquired immunodeficiency syndrome (AIDS), the method comprising administering to the subject an effective amount of vanadyl sulfate and an effective amount of micronized glyburide, wherein an effective amount of the vanadyl sulfate is about 60 mg to about 120 mg per day, and thereby improving one or more of the CD4 counts and CD4/CD8 lymphocyte cell ratios in the subject.

9. The method of claim 8, wherein the subject does not have diabetes mellitus.

10. The method of claim 8, wherein an effective amount of the micronized glyburide is from about 0.75 mg to about 12 mg per day.

11. A method of improving CD4 counts and CD4/CD8 lymphocyte cell ratios in a subject having human immunodeficiency virus (HIV) or acquired immunodeficiency syndrome (AIDS), the method comprising administering to the subject an effective amount of vanadyl sulfate and an effective amount of glyburide, thereby improving CD4 counts and CD4/CD8 lymphocyte cell ratios in the subject.

12. The method of claim 11, wherein the subject does not have diabetes mellitus.

13. The method of claim 11, wherein the glyburide is micronized.

* * * * *